United States Patent
Hu et al.

(10) Patent No.: US 12,305,225 B2
(45) Date of Patent: May 20, 2025

(54) POLYMERASE MUTANT AND APPLICATIONS THEREOF

(71) Applicants: Shanghai Zhongqi Biotechnology Co., Ltd., Shanghai (CN); Shanghai Xiansai Biotechnology Co., Ltd., Shanghai (CN)

(72) Inventors: Xuejun Hu, Shanghai (CN); Liqin Cao, Shanghai (CN)

(73) Assignees: Shanghai Zhongqi Biotechnology Co., Ltd., Shanghai (CN); Shanghai Xiansai Biotechnology Co., Ltd., Shanghai (CN)

( * ) Notice: Subject to any disclaimer, the term of this patent is extended or adjusted under 35 U.S.C. 154(b) by 0 days.

(21) Appl. No.: 18/885,661

(22) Filed: Sep. 15, 2024

(65) Prior Publication Data

US 2025/0011850 A1 Jan. 9, 2025

Related U.S. Application Data

(63) Continuation of application No. PCT/CN2023/095944, filed on May 24, 2023.

(30) Foreign Application Priority Data

May 9, 2022 (CN) .......................... 202210495569.4

(51) Int. Cl.
| | | |
|---|---|---|
| *C12N 15/09* | (2006.01) | |
| *C12N 9/12* | (2006.01) | |
| *C12Q 1/6806* | (2018.01) | |
| *C12Q 1/6844* | (2018.01) | |
| *C12Q 1/6869* | (2018.01) | |

(52) U.S. Cl.
CPC ......... *C12Q 1/6844* (2013.01); *C12N 9/1252* (2013.01); *C12Y 207/07007* (2013.01)

(58) Field of Classification Search
CPC .... C12N 9/1252; C12N 15/09; C12Q 1/6806; C12Q 1/6869; C12Q 1/6844; C12Y 207/07007

See application file for complete search history.

(56) References Cited

U.S. PATENT DOCUMENTS

| | | |
|---|---|---|
| 5,455,170 A | 10/1995 | Abramson et al. |
| 8,759,063 B2 | 6/2014 | Bauer et al. |
| 11,739,306 B2 | 8/2023 | Kurbanov |
| 2013/0149747 A1 | 6/2013 | Bauer et al. |
| 2021/0254035 A1 | 8/2021 | Kobayashi et al. |
| 2021/0269779 A1 | 9/2021 | Kurbanov |

FOREIGN PATENT DOCUMENTS

| | | |
|---|---|---|
| CN | 103987844 A | 8/2014 |
| CN | 110023493 A | 7/2019 |
| CN | 112703248 A | 4/2021 |

OTHER PUBLICATIONS

International Search Report, International Appl. No. PCT/CN2023/095944, Sep. 20, 2023.
Nancy J Schonbrunner et al. "Chimeric thermostable DNA polymerases with reverse transcriptase and attenuated 3-5' exonuclease activity," Biochemistry., vol. 45, No. 42, Oct. 24, 2006, Abstract and forward citations.
Written Opinion, International Appl. No. PCT/CN2023/095944, Sep. 20, 2023.

*Primary Examiner* — Maryam Monshipouri
(74) *Attorney, Agent, or Firm* — Central California IP Group, P.C.; Andrew D. Fortney

(57) ABSTRACT

A ZO5 DNA polymerase mutant and its application are disclosed. The ZO5 DNA polymerase mutant is obtained by mutation of a ZO5 wild-type polymerase, which has the amino acid sequence shown as SEQ ID NO:1. Mutation sites include E628K, I709L, E744R, and A745R. The polymerase mutant can expand its capacity for a variety of activities, including reverse transcriptase, and can catalyze reverse transcription-loop mediated isothermal amplification using an RNA template. The polymerase mutant after fusion of the binding peptide has a strong ability to resist interference, such as chocolate, peanut butter, milk, seafood, meat or egg, chocolate, pepper, blood, urine, humic acid, bile, tannin, melanin, indigo dye, plant materials, etc., and can effectively shorten the LAMP required time.

13 Claims, 3 Drawing Sheets

Specification includes a Sequence Listing.

POLYMERASE MUTANT AND APPLICATIONS THEREOF

CROSS-REFERENCE TO RELATED APPLICATIONS

This application is a continuation of International Pat. Appl. No. PCT/CN2023/095944, filed on May 24, 2023, which claims priority to Chinese Pat. Appl. No. 202210495569.4, filed on May 9, 2022, the contents of each of which are incorporated by reference herein in their entireties.

REFERENCE TO AN ELECTRONIC SEQUENCE LISTING

The contents of the electronic sequence listing SHCH-2200291-US_Revised_20240919.xml; Size: 29,523 bytes; and Date of Creation: Sep. 19, 2024) is incorporated herein by reference in its entirety.

TECHNICAL FIELD

The invention belongs to the field of molecular biology, in particular to a polymerase mutant and applications thereof.

BACKGROUND

Taq polymerase and Bst polymerase are two well-known heat-resistant DNA polymerases with 50% sequence homology in their crystal structures. Taq polymerase can catalyze the polymerase chain reaction (PCR) (this reaction requires that the enzyme must tolerate 94° C.), but Bst polymerase activity is at 65~70° C., so it cannot catalyze PCR. At the same time, Taq polymerase cannot replicate double-stranded DNA by replacing the previous DNA strand, and the 5'-endonuclease of Taq polymerase can degrade the replaced DNA. However, Bst polymerase can efficiently perform chain displacement without degradation, and is therefore commonly used to catalyze loop-mediated isothermal amplification (LAMP). But neither Taq polymerase nor Bst polymerase has reverse transcriptase (RT) activity, so it is usually necessary to combine a separate RT enzyme with them to complete RT-PCR (reverse transcriptase polymerase chain reaction) or a similar RT-LAMP.

In contrast, ZO5 DNA polymerase has strong reverse transcriptase polymerase chain reaction (RT-PCR) activity, but cannot replicate double-stranded DNA by chain replacement, and therefore cannot be used to catalyze loop-mediated isothermal amplification (LAMP).

In order to amplify an RNA target by PCR or LAMP, it is necessary to first reverse transcribe the RNA template into cDNA. In RT-PCR or RT-LAMP, it is difficult for mixed enzymes to exert their respective advantages, due to their different optimal reaction conditions. Typically, RT-PCR assays rely on non-heat-stable reverse transcriptase (RNA-dependent DNA polymerase) derived from thermophilic organisms for the initial cDNA synthesis step (RT). In PCR, an additional heat-stable DNA polymerase is required for cDNA amplification to tolerate the temperature increase required for nucleic acid denaturation.

SUMMARY

The present invention aims to provide a DNA polymerase mutant and its application.

To fulfill the purpose of the invention, the technical scheme adopted by the invention includes a ZO5 DNA polymerase mutant obtained by mutation of a ZO5 wild-type polymerase having the amino acid sequence shown in SEQ ID NO: 1, including the mutations E628K, I709L, E744R and A745R.

Preferably, the mutation sites also include E710K, E710L, E710N, E710Q, E710I, E710W, E710R, E710V or E710S.

Preferably, the polymerase mutant is obtained by truncating the wild-type polymerase.

Preferably, truncation is performed at site 282 of the wild-type polymerase.

Preferably, the polymerase mutant further includes a binding peptide bound or fused thereto.

Preferably, the binding peptide is selected from Sso 7d, Tm Csp, and Sac 7d.

Correspondingly, the invention further includes a polymerase mutant whose amino acid sequence is shown as SEQ ID NO: 3.

Correspondingly, the invention further includes a polymerase mutant whose amino acid sequence is shown as SEQ ID NO: 7.

Accordingly, the polymerase mutant is applied to PCR, RT-PCR, LAMP and RT-LMAP.

Correspondingly, the invention further includes reagents, test strips and kits containing the polymerase mutant(s).

The invention has the following beneficial effects. The use of engineered thermally active or thermally stable DNA polymerases for more efficient reverse transcription for RT-PCR or similar RT-LAMP assays has several potential benefits.

1. Enhanced reverse transcriptase activity together with the ability to use higher reverse transcriptase incubation temperatures, which allow relaxation of the RNA template secondary structure, and can lead to overall higher cDNA synthesis efficiency and detection sensitivity.
2. Higher temperature incubation may also increase specificity by reducing mismatches in the reverse transcription step.
3. Enzymes with improved reverse transcriptional efficiency can simplify assay design by reducing RT incubation time and/or enzyme concentration(s).
4. When dUTP and UNG are used (e.g., in or for PCR), non-specific extension products containing dUMP formed during PCR under non-rigorous conditions are degraded by UNG, and cannot be used as primers or templates. It is not possible to utilize the dUTP and UNG methods when using non-heat-stable reverse transcriptase (RNA-dependent DNA polymerase) derived from mesophilic organisms. However, the use of the present thermally-active or thermally-stable DNA polymerase for the reverse transcription step makes the reaction fully compatible with the use of a dUTP/uracil n-glycosylase (UNG) residue prevention system. In addition to providing a residue contamination control, the use of dUTP and UNG provides a "hot start" to reduce nonspecific amplification.

The polymerase mutant provided by the invention can expand its ability to perform a variety of activities, including reverse transcriptase (RT), and can catalyze reverse transcription-loop mediated isothermal amplification (RT-LAMP) using an RNA template. The polymerase mutant, after fusion of the binding peptide, also has a strong ability to resist adverse interference from contaminants, such as chocolate, peanut butter, milk, seafood, meat or egg, chocolate, pepper, blood, urine, humic acid, bile, tannin, melanin, indigo dye, plant materials, etc., and can effectively shorten the time for the LAMP process.

Contamination problems in RT-LAMP can also be solved by using the polymerase mutant provided by the invention. The biggest disadvantage of loop-mediated isothermal amplification method is that due to its very high sensitivity, once the lid is opened, it is easy to form aerosol pollution, and false positives become a serious problem. The problem can be solved when primers are prepared and diluted in an uncontaminated environment and added to the lid of each reaction tube. The remaining components of the reaction (buffer, DNA polymerase, MS2 template, etc.) can be added to the reaction tube with RNase-free DNase I and $MgCl_2$. The reaction can be conducted at room temperature for a period of time sufficient to degrade the DNA sample under the action of DNase I, and then the reaction tube can be gently moved to the thermal cycler with the primer still hanging on the lid. After heating on the heating block for some time, DNase I loses its activity. The reaction tube can then be removed from the heating block and mixed, then immediately returned to the heating block for incubation at a set temperature. The recognized pollution problem of the RT-LAMP reaction can be completely or partially overcome by using the above method.

DETAILED DESCRIPTION OF THE EMBODIMENTS

A DNA polymerase (ZO5 polymerase) mutant is provided. The DNA polymerase mutant is a mutated ZO5 wild-type polymerase. The amino acid sequence of the wild-type polymerase is given in SEQ ID NO: 1, and a corresponding DNA sequence (e.g., of the wild-type ZO5 polymerase) is given in SEQ ID NO: 2. The polymerase mutant was obtained by mutating E628K, I709L, E710K, E744R and A745R in the ZO5 wild-type polymerase. An alternative scheme preserves the E628K, I709L, E744R and A745R mutations, and further includes the mutation E710L, E710N, E710Q, E710I, E710W, E710R, E710V, or E710S for site 710.

The optimal scheme is as follows. The polymerase mutant is obtained by truncating the wild-type polymerase, and the truncation site can occur at any site of the full-length sequence, as long as the activity of ZO5 polymerase is preserved. It is preferred to truncate at site 282 of the wild-type polymerase of ZO5; that is, the first site of the truncated polymerase mutant corresponds to Site 282 of the wild-type polymerase amino acid sequence (SEQ ID NO: 1).

Another preferred scheme is that the polymerase mutant can further include one or more of Sso 7d, Tm Csp, Sac 7d and other binding peptides. Fusion binding peptides such as Sso7d and Sso7d binding to DNA will introduce a negative superhelix to DNA. Increasing the melting temperature of DNA can enhance the anti-interference ability of the present polymerase mutants and effectively shorten the LAMP time.

It should be understood that persons skilled in the art may, as needed, first perform mutations at the corresponding sites and then truncate the ZO5 polymerase, or first truncate the ZO5 polymerase and then perform mutations at the corresponding sites. Polymerase mutants can be obtained by directly synthesizing the corresponding amino acid sequence, or by synthesizing the corresponding DNA sequence and then translating it into amino acid sequence, or by truncating and/or mutating the wild-type polymerase.

Figure 1:
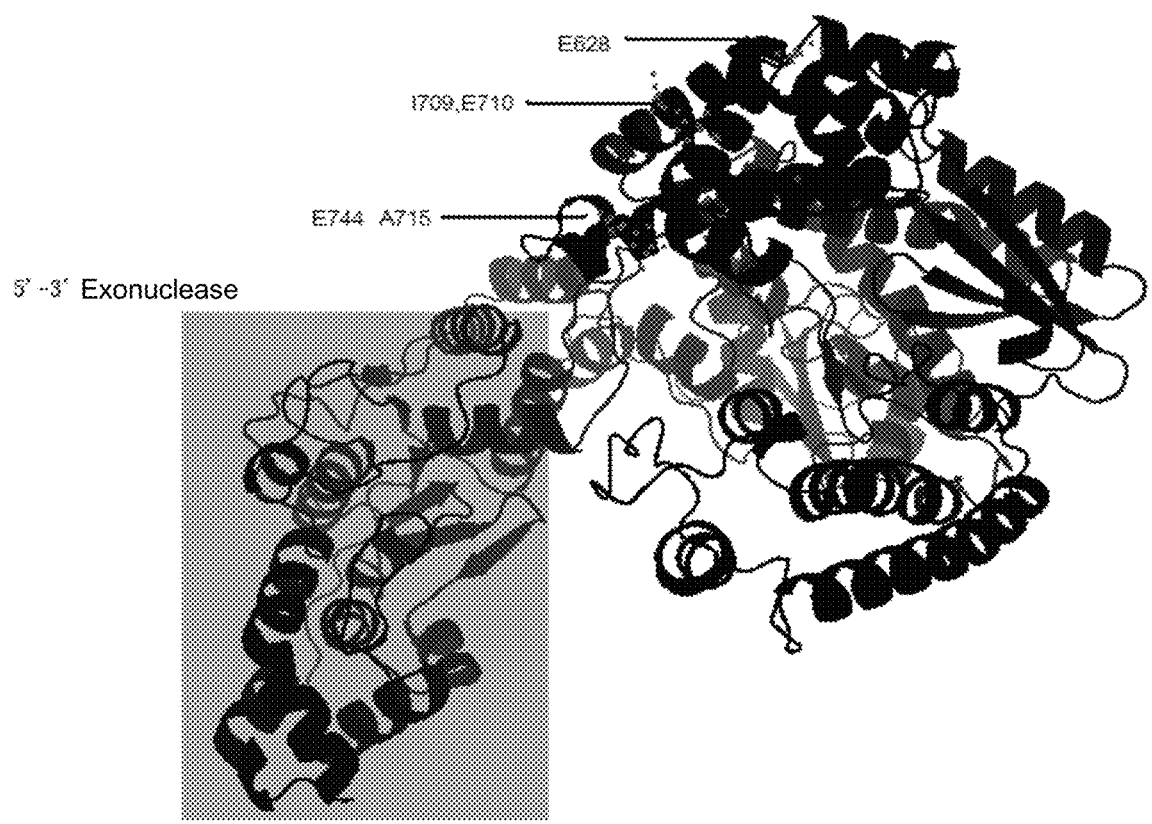
FIG. 1 shows the spatial structure diagram of wild-type polymerase and corresponding mutation sites.

After the wild-type polymerase is truncated at the Site 282 and mutated to include the E628K, I709L, E710K, E744R and A745R mutations, the amino acid sequence shown in SEQ ID NO: 3 was obtained for the polymerase mutant. The spatial structure diagram of wild-type polymerase and corresponding mutation sites is shown in FIG. 1.

The following is a clear and complete description of the technical scheme in embodiments of the invention. Obviously, the embodiments described are only part of the embodiments of the invention, but not all of the possible embodiments. Unless otherwise specified, the technical means used in the embodiments are conventional and well-known to those skilled in the art. All of the data presented herein are the average values obtained after at least 3 repetitions, and all of the data obtained from each repetition used in the average value calculation are valid data.

Example 1: Expression and Purification of Polymerase Mutants

Step (1): Preparation of a polymerase mutant gene expression vector. The plasmid template of the ZO5 wild-type polymerase gene (e.g., including SEQ ID NO: 2) was selected, and E628K-F, E628K-R, IE709LK-F, IE709LK-R, EA744RR-F, and EA744RR-R were used as mutation primers. ZO5-NdeI-F and ZO5-SalI-R were used as truncated PCR primers. 1 μL of the primers (10 μM) were added to a 50 μL reaction system and mixed with a 50 μL PCR reaction system, including 10×buffer (100 mM KCl, 100 mM $(NH_4)_2SO_4$, 200 mM Tris-HCl [pH=8.8], 20 mM $MgSO_4$, 5 μL 1% TritonX-100, 1 mg/mL BSA), 3 μL 2 mM dNTP, and 1 μL of the KOD enzyme. A total of 25 amplification cycles were performed according to the following procedure: 95° C., 1 min; 95° C., 30 s; 60° C., 30 s; 68° C., 2 min; 68° C., 5 min; and then storing at 4° C. The amplification primers are shown in Table 1. IE709LK stands for I709L, and E710K and EA744RR stand for E744R and A745R.

TABLE 1

| Sequence of amplified primers | |
|---|---|
| Primer | Sequence |
| E628K-F | CTCATCTGAGCGGTGACAAGAACCTGATTCGTGTGTTTCA (SEQ ID NO: 9) |
| E628K-R | CTTTGTGTGCTTAGTCCAAGAACAGTGGCGAGTCTACTCG GTCTTG (SEQ ID NO: 10) |
| IE709LK-F | GAAAGTTCGTGCGTGGCTCAAAAAAACCCTGGAAGAAGGT CG (SEQ ID NO: 11) |
| IE709LK-R | GAAGAAGGTCCCAAAAAAACTCGGTGCGTGCTTGAAAGCC CTTCCTG (SEQ ID NO: 12) |
| EA744RR-F | GTTAAATCTGTACGCCGCCGTGCTGAACGTATGGCATTTA ACATG (SEQ ID NO: 13) |

TABLE 1-continued

Sequence of amplified primers

| Primer | Sequence |
|---|---|
| EA744RR-R | TACGGTATGCAAGTCGTGCCGCCGCATGTCTAAATTGTGC GCGCAAG (SEQ ID NO: 14) |
| ZO5-Nde1-F | TAAGAAGGAGATATACATATGGGTCTGCTGCACGAGTTTG GCCTGC (SEQ ID NO: 15) |
| ZO5-Sal1-R | GCTACCACCGCCCCCGTCGACACCTTTAGCGCTCAGCCAA TCTTCAC (SEQ ID NO: 16) |

The amplified reaction system was subject to electrophoresis with 1.2% agarose gel at 150 V for 30 min, and the target strip was recovered. The pET 42a vector treated with Nde1 and Xho1 was connected by an enzyme-ligating method, and the clone was selected for sequencing. The DNA sequence obtained was SEQ ID NO: 4. Seamless cloning was adopted to connect the pET Sso 7d vector treated with Nde1 and Sal1 (from Shanghai Xiansai Biotechnology Co., Ltd., containing binding peptide Sso 7d), then the clone was selected and sequenced. The obtained DNA sequence is SEQ ID NO: 6.

Step (2): Expression and purification of the polymerase mutants. The two plasmid vectors obtained in step (1) were respectively introduced into BL21 (DE3) and cultured overnight in an LB medium containing antibiotics at 37° C., 160 r/min. *Escherichia coli* bodies obtained after cloning-induced expression were selected respectively. Two polymerase mutants were obtained after purification. The amino acid sequence obtained using SEQ ID NO: 4 was SEQ ID NO: 5, and named ZO5 L1. SEQ ID NO: 6 corresponds to the amino acid sequence SEQ ID NO: 7, named ZO5 L2. To be clear: In the amino acid sequences of ZO5 L1 and ZO5 L2 (SEQ ID NO: 5, SEQ ID NO: 7), "Leu Glu His His His His His His His (His)" at the end of the sequences came from the carrier, which had no effect on the performance of the polymerase mutant. These end sequences can be kept or omitted. ZO5 L2 is based on ZO5 L1, but with the binding peptide Sso 7d.

Example 2: RT-PCR Using Polymerase Mutants

Using the DNA sequence of MS2 in the Chinese patent publication no. 113846146A as a template (the DNA sequence is shown in SEQ ID NO: 8), each hole contains 3 μL ZO5 L1 and ZO5 L2 enzymes diluted 10 times with buffer solution, and ZO5 wild-type polymerase is used as a control. PCR and RT-PCR were performed. In each group, the buffer contains 20 mM Tris-HCl (pH=8), 100 mM KCl, 0.1 mM EDTA, and 0.1% Tween-2. They were added to 12 μL RT-PCR premixes as shown in Table 2 for thermal cycling. Heat cycle conditions included 50° C., 2 minutes (the "UNG" step); 65° C., 2 minutes (the "RT" step); 5 cycles at 94° C., 15 seconds; then 62° C., 30 seconds; then 45 cycles at 91° C. for 15 seconds; then 62° C. for 30 seconds.

TABLE 2

RT-PCR premixes

| Constituent | Concentration |
|---|---|
| Tris-HCl (pH = 8) | 50 mM |
| KOAc | 60 mM |

TABLE 2-continued

RT-PCR premixes

| Constituent | Concentration |
|---|---|
| glycerin | 5% (v/v) |
| DMSO | 2% (v/v) |
| $MgCl_2$ | 2 mM |
| primer 1 | 200 nM |
| primer 2 | 200 nM |
| dUTP | 400 nM |
| dATP | 200 nM |
| dCTP | 200 nM |
| dGTP | 200 nM |
| UNG | 2 U/μL |
| MS2 RNA Template | 50 ng |

Figure 2:
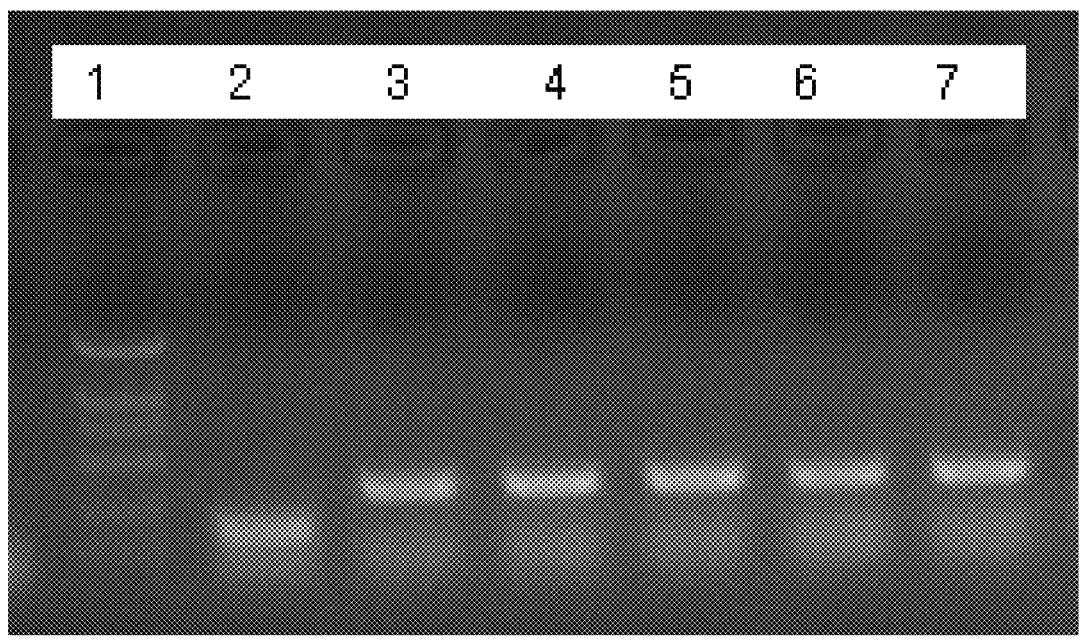
FIG. 2 shows the results of an RT-PCR experiment using one of the present polymerase mutants.

The result is shown in FIG. 2. In FIG. 2, lane 1 represents DL2000 DNA markers, lane 2 is the blank/control, lanes 3 and 4 are ZO5 L1, lanes 5 and 6 are ZO5 L2, and lane 7 is ZO5 wild-type polymerase. The results showed that ZO5 L1 and ZO5 L2 retained the basic properties of ZO5 wild-type polymerase for RT-PCR.

Example 3: Lamp Reaction Temperature Test of Polymerase Mutants

Primers were designed to detect MS2 specific genes (the MS2 gene sequence is shown in SEQ ID NO: 8), the specific sequence of designed MS2 primers is shown in Table 3, and the reaction system is shown in Table 4.

TABLE 3

Sequence of MS2 primers

| Primers | Sequences (5' to 3') |
|---|---|
| MS2-BIP | GCACGTTCTCCAACGGTGCTGGTTGCTTGTTCAGCGAACT (SEQ ID NO: 17) |
| MS2-FIP | GCCCAAACAACGACGATCGGTAAAACCAGCATCCGTAGCCT (SEQ ID NO: 18) |
| MS2-LB | TGCAGGATGCAGCGCCTTA (SEQ ID NO: 19) |
| MS2-LF | CCAGAGAGGAGGTTGCCAA (SEQ ID NO: 20) |
| MS2-B3 | CAATAGAGCCGCTCTCAGAG (SEQ ID NO: 21) |
| MS2-F3 | TGTCATGGGATCCGGATGTT (SEQ ID NO: 22) |

TABLE 4

Reaction system

| Samples | Concentration | Amount added (μL) |
|---|---|---|
| MS2 template | 1 ng/uL | 1 |
| MS2-BIP | 10 μm | 1.6 |
| MS2-FIP | 10 um | 1.6 |
| MS2-LF | 10 um | 0.8 |
| MS2-LB | 10 um | 0.8 |
| MS2-F3 | 10 um | 0.2 |
| MS2-B3 | 10 um | 0.2 |
| dNTP/dUTP Mixture | 25 mM | 0.8 |
| Mg2+ | 100 mM | 1 |
| 10× buffer | \ | 2.5 |
| DNA polymerase | \ | 1 |
| Eva Green Dye | 10× | 2.5 |
| Water | \ | 10.5 |
| UDG | \ | 1 |
| Bulk volume | \ | 25 uL |

The above reaction system was carried out in a Bio-Rad CFX Connect™ PCR system using a SYBR program, and the Plate Read was performed at 60° C. and 30 s for 120 cycles. The Gradient Range was set to 15.0. LAMP expansion was performed at A: 75.0° C., B: 74.2° C., C: 72.5° C., D: 69.5° C., E: 65.9° C., F: 63.0° C., G: 61.0° C. and H: 60.0° C. The results are shown in Table 5.

TABLE 5

Comparison table of temperature experiment results

| Temperature | ZO5 L2 Cp | ZO5 L1 Cp |
| --- | --- | --- |
| 75.0° C. | 50.2 | 55.2 |
| 74.2° C. | 37.6 | 40.6 |
| 72.5° C. | 31.6 | 35.7 |
| 69.5° C. | 33.2 | 39.3 |
| 65.9° C. | 55.2 | 60.4 |
| 63.0° C. | 70.2 | N/A |
| 61.0° C. | N/A | N/A |
| 60.0° C. | N/A | N/A |

The results showed that the enzyme activity of the polymerase mutant was the best at 72° C., and the reaction rate of ZO5 L2 was faster than that of ZO5 L1. The results further showed that the polymerase mutant can use a conventional dNTP/dUTP mixture to conduct the experiment, which can reduce or prevent contamination.

Example 4: Rt-Lamp Experiment of Polymerase Mutants

Using the conditions of Example 3, a gradient 10-fold dilution of the RNA template for MS2 was prepared in a Bio-Rad CFX Connect™ PCR system using a SYBR program. LAMP extension was then performed at 50° C. for 2 minutes (the "UNG" step); 65° C. for 2 minutes (the "RT" step); 72° C., 30 seconds for 1 cycle, and Plate Read (72° C., 30 seconds), 120 cycles. The results are shown in Table 6 and FIG. 3.

TABLE 6

LAMP results of ZO5 L2 at different template RNA concentrations

| Template RNA concentrations | ZO5 L2 Cp |
| --- | --- |
| 8 ng | 30.13 |
| 800 pg | 38.38 |
| 80 pg | 46.56 |
| 8 pg | 54.70 |
| 800 fg | 61.03 |
| 80 fg | 67.44 |
| 8 fg | 80.79 |
| 0 | N/A |

Figure 3:
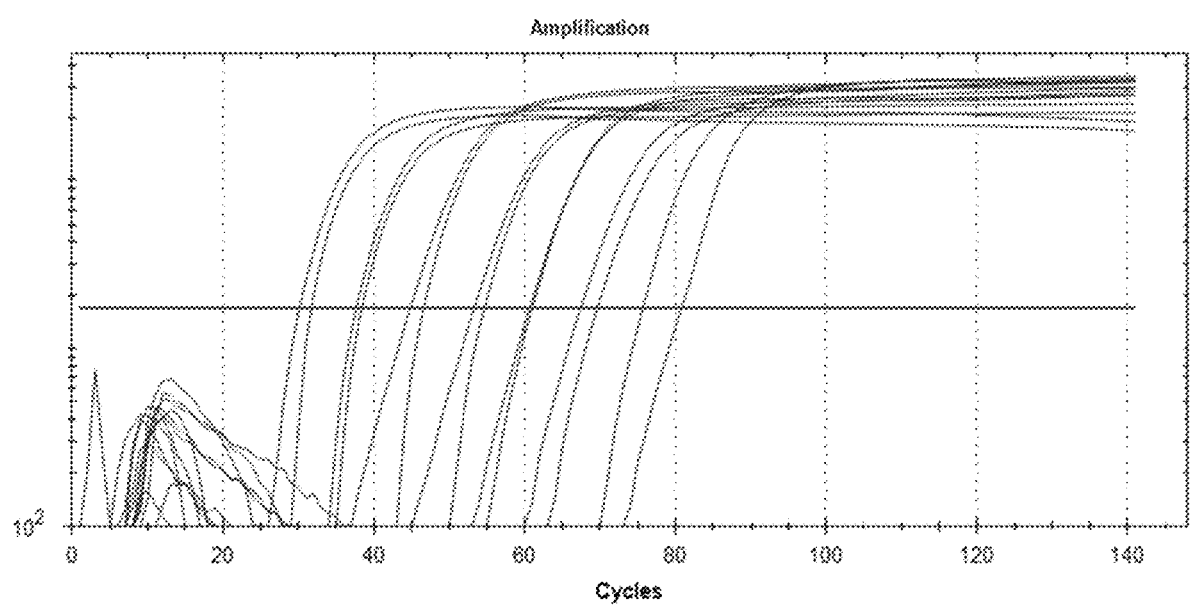
FIG. 3 shows the results of an RT-LAMP experiment using one of the present polymerase mutants.

The results show that ZO5 L2 has better reaction speed, and the RT-LAMP experiment on ZO5 L2 shows very good RT-LAMP performance as shown in Table 6 and FIG. 3.

Example 5: Lamp Immunity Experiment of Polymerase Mutant ZO5 L2

Under the conditions of Example 4, the DNA template of MS2 (200 pg) was added into a reaction tube, and the reaction was carried out in a Bio-Rad CFX Connect™ PCR system using a SYBR program, with a cycle of 72° C., 30 seconds and Plate Read, 120 cycles, setting multiple processes. LAMP expansion was performed by adding different interfering substances (10% urine, 10% whole blood, 10% E. coli breakdown solution). The results are shown in FIG. 4.

Figure 4:
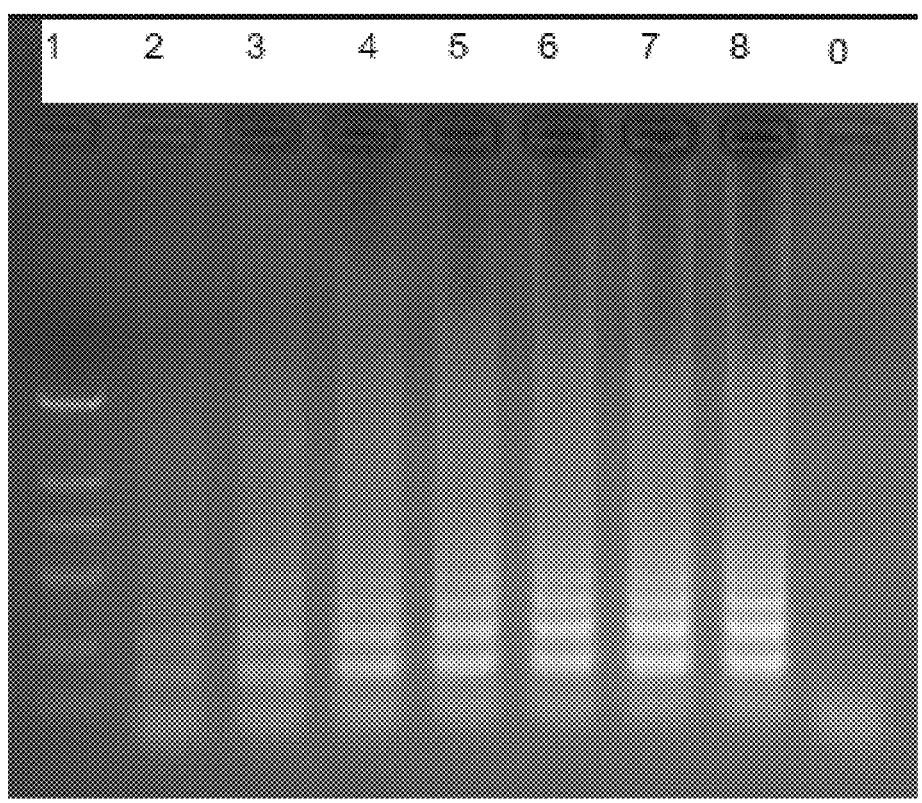
FIG. 4 shows results of a LAMP anti-interference experiment using the polymerase mutant ZO5 L2.

In FIG. 4, lane 1 is DL2000 DNA markers, lane 0 is a blank/control, lanes 2 and 3 are treatments with 10% urine added, lanes 4 and 5 are treatments with 10% whole blood added, lanes 6 and 7 are treatments with 10% E. coli breakdown solution added, and lane 8 is a control treatment with an amount of water equal to the volume of interfering substance added. The results showed that the polymerase mutant ZO5 L2 had good immunity ability.

Example 6: Mutation of the Amino Acid at Position 710 of the Polymerase Mutant ZO5

Using the ZO5 L2 polymerase with the mutation at site 710 (e.g., E710K, E710L, E710N, E710Q, E710I, E710W, E710R, E710V or E710S), the experiment of Example 4 with a template RNA concentration or mass of 80 pg was repeated, with other conditions unchanged. In addition, 10% whole blood was used as the interfering substance, and the results are shown in Table 7.

TABLE 7

Comparison table of performance display of polymerase mutant ZO5 after amino acid mutation at Site 710

| Site 710 mutation | RT-LAMP cp | LAMP immunity experiments active cp |
| --- | --- | --- |
| E710K | 67.66 | 68.45 |
| E710L | 67.85 | 67.52 |
| E710N | 69.2 | 69.82 |
| E710Q | 68.51 | 69.52 |
| E710I | 67.39 | 68.27 |
| E710W | 70.58 | 66.31 |
| E710R | 69.25 | 67.34 |
| E710V | 68.01 | 71.06 |
| E710S | 67.23 | 69.54 |

The results showed that the mutations E710L, E710N, E710Q, E710I, E710W, E710R, E710V and E710S at Site 710 had the same RT-LAMP ability and anti-interference ability as E710K.

The above embodiments describes only various methods and examples of the invention and do not limit the scope of the invention. Under the premise of not deviating from the design or spirit of the invention, all kinds of deformations, variations, modifications and replacements of the technical scheme of the invention made by ordinary technicians in the field shall fall within the scope of protection determined by the claims of the invention.

What is claimed is:

1. A ZO5 DNA polymerase, having an amino acid sequence shown in SEQ ID NO: 1, with mutations E628K, I709L, E744R and A745R.

2. A polymerase, having an amino acid sequence shown in SEQ ID NO: 3.

3. A polymerase, having an amino acid sequence shown in SEQ ID NO: 7.

4. Reagents, test strips and kits containing the polymerase in claim 1.

5. A reagent containing the polymerase in claim 1.

6. A test strip containing the polymerase in claim 1.

7. A kit containing the polymerase in claim 1.

8. A reagent containing the polymerase in claim 2.

9. A test strip containing the polymerase in claim 2.

10. A kit containing the polymerase in claim 2.

11. A reagent containing the polymerase in claim 3.

12. A test strip containing the polymerase in claim 3.

13. A kit containing the polymerase in claim 3.

* * * * *

SEQUENCE LISTING

```
Sequence total quantity: 22
SEQ ID NO: 1          moltype = AA  length = 834
FEATURE               Location/Qualifiers
source                1..834
                      mol_type = protein
                      organism = Thermus sp.
SEQUENCE: 1
MKAMLPLFEP KGRVLLVDGH HLAYRTFFAL KGLTTSRGEP VQAVYGFAKS LLKALKEDGY    60
KAVFVVFDAK APSFRHEAYE AYKAGRAPTP EDFPRQLALI KELVDLLGFT RLEVPGFEAD   120
DVLATLAKKA EREGYEVRIL TADRDLYQLV SDRVAVLHPE GHLITPEWLW EKYGLKPEQW   180
VDFRALVGDP SDNLPGVKGI GEKTALKLLK EWGSLENILK NLDRVKPESV RERIKAHLED   240
LKLSLELSRV RSDLPLEVDF ARRREPDREG LRAFLERLEF GSLLHEFGLL EAPAPLEEAP   300
WPPPEGAFVG FVLSRPEPMW AELKALAACK EGRVHRAKDP LAGLKDLKEV RGLLAKDLAV   360
LALREGLDLA PSDDPMLLAY LLDPSNTTPE GVARRYGGEW TEDAAHRALL AERLQQNLLE   420
RLKGEEKLLW LYQEVEKPLS RVLAHMEATG VRLDVAYLKA LSLELAEEIR RLEEEVFRLA   480
GHPFNLNSRD QLERVLFDEL RLPALGKTQK TGKRSTSAAV LEALREAHPI VEKILQHREL   540
TKLKNYYVDP LPGLVHPRTG RLHTRFNQTA TATGRLSSSD PNLQNIPIRT PLGQRIRRAF   600
VAEAGWALVA LDYSQIELRV LAHLSGDENL IRVFQEGKDI HTQTASWMFG VSPEAVDPLM   660
RRAAKTVNFG VLYGMSAHRL SQELAIPYEE AVAFIERYFQ SPPKVRAWIE KTLEEGRKRG   720
YVETLFGRRR YVPDLNARVK SVREAAERMA FNMPVQGTAA DLMKLAMVKL FPHLREMGAR   780
MLLQVHDELL LEAPQARAEE VAALAKEAME KAYPLAVPLE VEVGIGEDWL SAKG         834

SEQ ID NO: 2          moltype = DNA  length = 2502
FEATURE               Location/Qualifiers
source                1..2502
                      mol_type = genomic DNA
                      organism = Thermus sp.
SEQUENCE: 2
atgaaagcga tgctgccgct gttcgaaccg aaaggtcgtg ttctgctggt tgatggccac    60
cacctggcgt accgtacctt cttcgcgctg aaaggtctga ccacttctcg tggtgaaccg   120
gtacaggcgg tctacggctt cgctaaatcc ctgctgaaag cactgaaaga gatgggctat   180
aaagctgtat ttgtagtatt tgacgccaaa gcgccgtcct tccgtcatga agcttacgaa   240
gcgtacaaag caggccgtgc gccgaccccg gaagatttcc cgcgccagct ggcgctgatt   300
aaagaactgg ttgatctgct gggtttcact cgtcttgaag ttccgggttt cgaagcggat   360
gatgttctgg ctaccctggc gaaaaaagcg gaacgtgaag gctacgaagt gcgtatcctg   420
accgctgatc gtgacctgta ccagctggtg tctgatcgcg ttgctgtgct gcatccgaaa   480
ggccacttga tcaccccgga atggctgtgg gaaaaatacg gtctgaaacc ggaacagtgg   540
gtggatttcc gcgcgctggt tggcgacccg agcgacaatc tgccgggcgt gaaaggtatc   600
ggcgaaaaaa ccgcactgaa actgctgaaa gaatggggtt cgctggaaaa catcctgaaa   660
aacctggacc gcgtgaaacc ggaatccgtt cgtgaacgca ttaaagcaca cctggaagat   720
ctgaaactga gcttggaact gagccgtgta cgctctgacc tgccgctcga agtagatttc   780
gctcgtcgtc gtgaacctga tcgtgaaggc ctgcgcgcgt tcctggaacg cctggaattc   840
ggtagcctgc tgcacgagtt tggcctgctg gaggcgccag cgccgctgga agaagcaccg   900
tggccgccac cggaaggtgc gttcgtaggt ttttgtcctgt cccgtccgga accgatgtgg   960
gccgaactta aggctctggc agcttgcaaa gaaggccgtg tccaccgcgc taaagatcca  1020
ctggcgggcc ttaaagacct gaaagaagtt cgcggccttc tggctaaaga cctggcggtt  1080
ctggcgctgc gtgaaggtct ggatctcgcg cctagcgatg acccgatgct gttggcatac  1140
ctgctggacc cgagtaacac caccccggaa ggcgttgccc gtcgctatgg cggcgaatgg  1200
actgaggatg ctgcccaccg cgcgctgctc gcagaacgcc tgcagcagaa cttgctggag  1260
cgcttgaaaa gtgaagaaaa actgctttgg ctgtatcagg aagttgaaaa accgctgagc  1320
cgcgttctgg cacacatgga agcgactggg gttcgtctgg acgtggcgta cctgaaagct  1380
ctgtccctgg aactggctga gaaaatccgc cgcttggagg aagaagtttt ccgcctggcg  1440
ggccacccgt tcaacctgaa cagccgcgac caactggaac gtgttctgtt tgatgaactg  1500
cgcctgccgg ctctgggcaa aacccaaaaa accggtaagc gttctacttc cgccgcggtt  1560
ctggaagcac tgcgcgaagc cacccgattg tggaaaaaaa ttctgcagca ccgtgaactg  1620
actaaactga aaaactacta tgttgacccg ctgccgggcc tggttcaccc acgtactggt  1680
cgcctgcata cccgtttcaa ccagaccgca actgccaccg gcgtttgtc gtccagcgat  1740
ccgaacctgc agaatatccc gatccgcacc ccgctgggtc agcgtatccg tcgcgccttc  1800
gtcgcagaag ccgttgggc gcttgttgcg ctggactata gccagattga actgcgtgtt  1860
ctggctcatc tgagcggtga cgagaacctg attcgtgtgt tcaagaagg caaagatatc  1920
cacacccaga ccgctagctg gatgtttggt gtgagcccgg aagcggttga tccactgatg  1980
cgccgcgcgg cgaaaacggt gaactttggt gttctgtacg gtatgagcgc gcaccgtttg  2040
tctcaggaac tggctatccc gtacgaagaa gcagttgcgt tcattgaacg ttatttccag  2100
tccttcccga aagttcgtgc gtggatcgaa aaaccctgg aagaaggtcg taaacgtggt  2160
tacgttgaaa ccctgttcgg ccgccgtcgc tatgtgccga acctgaacgc gcgtgttaaa  2220
tctgtacgcg aagcagctga acgtatggca tttaacatgc cggtcagggg taccgcggct  2280
gacctgatga aactggcgat ggttaaactg ttcccgcacc tgcgcgaaat gggcgcgcgt  2340
atgctgctgc aggtgcacga cgaactgctg ctggaagcac gcaggcgcg tgcagaagaa  2400
gtggcggcgc tggcaaaaga agccatgaaa aagcatacc cgctggctgt gccgctggaa  2460
gttgaagtgg gtatcggtga agattggctg agcgctaaag gt                    2502

SEQ ID NO: 3          moltype = AA  length = 554
FEATURE               Location/Qualifiers
source                1..554
                      mol_type = protein
                      organism = Synthetic construct
SEQUENCE: 3
MGLLHEFGLL EAPAPLEEAP WPPPEGAFVG FVLSRPEPMW AELKALAACK EGRVHRAKDP    60
```

```
LAGLKDLKEV RGLLAKDLAV LALREGLDLA PSDDPMLLAY LLDPSNTTPE GVARRYGGEW    120
TEDAAHRALL AERLQQNLLE RLKGEEKLLW LYQEVEKPLS RVLAHMEATG VRLDVAYLKA    180
LSLELAEEIR RLEEEVFRLA GHPFNLNSRD QLERVLFDEL RLPALGKTQK TGKRSTSAAV    240
LEALREAHPI VEKILQHREL TKLKNYYVDP LPGLVHPRTG RLHTRFNQTA TATGRLSSSD    300
PNLQNIPIRT PLGQRIRRAF VAEAGWALVA LDYSQIELRV LAHLSGDKNL IRVFQEGKDI    360
HTQTASWMFG VSPEAVDPLM RRAAKTVNFG VLYGMSAHRL SQELAIPYEE AVAFIERYFQ    420
SFPKVRAWLK KTLEEGRKRG YVETLFGRRR YVPDLNARVK SVRRRAERMA FNMPVQGTAA    480
DLMKLAMVKL FPHLREMGAR MLLQVHDELL LEAPQARAEE VAALAKEAME KAYPLAVPLE    540
VEVGIGEDWL SAKG                                                    554

SEQ ID NO: 4            moltype = DNA   length = 1662
FEATURE                 Location/Qualifiers
source                  1..1662
                        mol_type = other DNA
                        organism = synthetic construct
SEQUENCE: 4
atgggtctgc tgcacgagtt tggcctgctg gaggcgccag cgccgctgga agaagcaccg     60
tggccgccac cggaaggtgc gttcgtaggt tttgtcctgt cccgtccgga accgatgtgg    120
gccgaactta aggctctggc agcttgcaaa gaaggccgtg tccaccgcgc taaagatcca    180
ctggcgggcc ttaaagacct gaaagaagtt cgcggccttc tggctaaaga cctggcggtt    240
ctggcgctgc gtgaaggtct ggatctcgcg cctagcgatg acccgatgct gttggcatac    300
ctgctggacc cgagtaacac caccccggaa ggcgttgctc gtcgtatgg cggcgaatgg    360
actgaggatg ctgcccaccg cgcgctgctc gcagaacgcc tgcagcagaa cttgctggag    420
cgcttgaaag gtgaagaaaa actgctttgg ctgtatcagg aagttgaaaa accgctgagc    480
cgcgttctgg cacacatgga agcgactggc gttcgtctgg acgtggcgta cctgaaagct    540
ctgtccctga aactggctga gaaaatccgc cgcttggaag aagaagttt ccgcctggcg    600
ggccacccgt tcaacctgaa cagccgcgac caactggaac gtgttctgtt tgatgaactg    660
cgcctgccgg ctctgggcaa accaaaaa accgtaagc gttctacttc cgccgcggtt    720
ctggaagcac tgcgcgaagc acccgatt gtggaaaaaa ttctgcagca ccgtgaactg    780
actaaactga aaaactacta tgttgacccg ctgccgggcc tggttcaccc actgactgt     840
cgcctgcata cccgtttcaa ccagaccgca actgccaccg gccgtttgtc gtccagcgat    900
ccgaacctgc agaatatccc gatccgcacc ccgctgggtc agcgtatccg tcgcgccttc    960
gtcgcagaag ccggttgggc gcttgttgcg ctggactata gccagattga actgcgtgtt   1020
ctggctcatc tgagcggtga caagaaccgc attcgtgtgt ttcaagaagg caagagatatc   1080
cacaccagac cgctagctg gatgtttggt gtgagcccgg aagcggttga tccactgatg   1140
cgccgcgcgg cgaaaacggt gaactttggt gttctgtacg gtatgagcgc gcaccgtttg   1200
tctcaggaac tggctatccc gtacgaagaa gcagttgcgt tcattgaacg ttatttccag   1260
tccttcccga agttcgtgc gtggctcaaa aaaaccctgg aagaaggtcg taaacgtggt   1320
tacgttgaaa ccctgttcgg ccgccgtcgc tatgtgcgaa acctgaacgc gcgtgttaaa   1380
tctgtacgcc gccgtgctga acgtatggca tttaacatgc cggtgcaggg taccgcggct   1440
gacctgatga aactggcgat ggttaaactg ttcccgcacc tgcgcgaaat gggcgcgcgt   1500
atgctgctgc aggtgcacga cgaactgctg ctggaagcac gcaggcgcg tgcagaagaa   1560
gtggcggcgc tggcaaaaga agccatgaaa aagcatacc gctggctgt gccgctgaa   1620
gttgaagtgg gtatcggtga agattggctg agcgctaaag gt                    1662

SEQ ID NO: 5            moltype = AA   length = 563
FEATURE                 Location/Qualifiers
source                  1..563
                        mol_type = protein
                        organism = synthetic construct
SEQUENCE: 5
MGLLHEFGLL EAPAPLEEAP WPPPEGAFVG FVLSRPEPMW AELKALAACK EGRVHRAKDP    60
LAGLKDLKEV RGLLAKDLAV LALREGLDLA PSDDPMLLAY LLDPSNTTPE GVARRYGGEW    120
TEDAAHRALL AERLQQNLLE RLKGEEKLLW LYQEVEKPLS RVLAHMEATG VRLDVAYLKA    180
LSLELAEEIR RLEEEVFRLA GHPFNLNSRD QLERVLFDEL RLPALGKTQK TGKRSTSAAV    240
LEALREAHPI VEKILQHREL TKLKNYYVDP LPGLVHPRTG RLHTRFNQTA TATGRLSSSD    300
PNLQNIPIRT PLGQRIRRAF VAEAGWALVA LDYSQIELRV LAHLSGDKNL IRVFQEGKDI    360
HTQTASWMFG VSPEAVDPLM RRAAKTVNFG VLYGMSAHRL SQELAIPYEE AVAFIERYFQ    420
SFPKVRAWLK KTLEEGRKRG YVETLFGRRR YVPDLNARVK SVRRRAERMA FNMPVQGTAA    480
DLMKLAMVKL FPHLREMGAR MLLQVHDELL LEAPQARAEE VAALAKEAME KAYPLAVPLE    540
VEVGIGEDWL SAKGLEHHHH HHH                                           563

SEQ ID NO: 6            moltype = DNA   length = 1905
FEATURE                 Location/Qualifiers
source                  1..1905
                        mol_type = other DNA
                        organism = synthetic construct
SEQUENCE: 6
atgggtctgc tgcacgagtt tggcctgctg gaggcgccag cgccgctgga agaagcaccg     60
tggccgccac cggaaggtgc gttcgtaggt tttgtcctgt cccgtccgga accgatgtgg    120
gccgaactta aggctctggc agcttgcaaa gaaggccgtg tccaccgcgc taaagatcca    180
ctggcgggcc ttaaagacct gaaagaagtt cgcggccttc tggctaaaga cctggcggtt    240
ctggcgctgc gtgaaggtct ggatctcgcg cctagcgatg acccgatgct gttggcatac    300
ctgctggacc cgagtaacac caccccggaa ggcgttgctc gtcgtatgg cggcgaatgg    360
actgaggatg ctgcccaccg cgcgctgctc gcagaacgcc tgcagcagaa cttgctggag    420
cgcttgaaag gtgaagaaaa actgctttgg ctgtatcagg aagttgaaaa accgctgagc    480
cgcgttctgg cacacatgga agcgactggc gttcgtctgg acgtggcgta cctgaaagct    540
ctgtccctga aactggctga gaaaatccgc cgcttggagg aagaagttt ccgcctggcg    600
ggccacccgt tcaacctgaa cagccgcgac caactggaac gtgttctgtt tgatgaactg    660
```

```
cgcctgccgg ctctgggcaa aacccaaaaa accggtaagc gttctacttc cgccgcggtt   720
ctggaagcac tgcgcgaagc acacccgatt gtgaaaaaa ttctgcagca ccgtgaactg   780
actaaactga aaaactacta tgttgacccg ctgccgggcc tggttcaccc acgtactggt   840
cgcctgcata cccgtttcaa ccagaccgca actgccaccg ccgtttgtc gtccagcgat   900
ccgaacctgc agaatatccc gatccgcacc ccgctggcgc agcgtatccg tcgcgccttc   960
gtcgcagaag ccggttgggc gcttgttgcg ctggactata gccagattga actgcgtgtt  1020
ctggctcatc tgagcggtga caagaacctg attcgtgtgt ttcaagaagg caaagatatc  1080
cacacccaga ccgctagctg gatgtttggt gtgagcccgg aagcggttga tccactgatg  1140
cgccgcgcg cgaaaacggt gaactttggt gttctgtacg gtatgagcgc gcaccgtttg  1200
tctcaggaac tggctatccc gtacgaagaa gcagttgcgt tcattgaacg ttatttccag  1260
tccttcccga aagttcgtgc gtggctcaaa aaaccctgg aagaaggtcg taaacgtggt  1320
tacgttgaaa ccctgttcgg ccgccgtcgc tatgtgccgg acctgaacgc gcgtgttaaa  1380
tctgtacgcc gccgtgctga acgtatggca tttaacatgc cggtgcaggg taccgcggct  1440
gacctgatga aactggcgat ggttaaactg ttcccgcacc tgcgcgaaat gggcgcgcgt  1500
atgctgctgc aggtgcacga cgaactgctg ctggaagcac cgcaggcgcg tgcagaagaa  1560
gtggcggcgc tggcaaaaga agccatgaaa aaagcatacc cgctggctgt gccgctggaa  1620
gttgaagtgg gtatcggtga agattggctg agcgctaaag tgtcgacgg gggcggtggt  1680
agcgcaaccg ttaaattcaa atacaaaggt gaagaaaaag aagttgatat tagcaaaatc  1740
aagaaagttt ggcgtgttgg aaaaatgatt agctttacct atgatgaagg tggtgggaaa  1800
accggtcgtg gtgcagttag cgaaaaagat gcaccgaaag aactgttaca aatgctggaa  1860
aaacagaaga aactcgagca ccaccaccac caccaccac actaa               1905

SEQ ID NO: 7            moltype = AA   length = 634
FEATURE                 Location/Qualifiers
source                  1..634
                        mol_type = protein
                        organism = synthetic construct
SEQUENCE: 7
MGLLHEFGLL EAPAPLEEAP WPPPEGAFVG FVLSRPEPMW AELKALAACK EGRVHRAKDP   60
LAGLKDLKEV RGLLAKDLAV LALREGLDLA PSDDPMLLAY LLDPSNTTPE GVARRYGGEW  120
TEDAAHRALL AERLQQNLLE RLKGEEKLLW LYQEVEKPLS RVLAHMEATG VRLDVAYLKA  180
LSLELAEEIR RLEEEVFRLA GHPFNLNSRD QLERVLFDEL RLPALGKTQK TGKRSTSAAV  240
LEALREAHPI VEKILQHREL TKLKNYYVDP LPGLVHPRTG RLHTRFNQTA TATGRLSSSD  300
PNLQNIPIRT PLGQRIRRAF VAEAGWALVA LDYSQIELRV LAHLSGDKNL IRVFQEGKDI  360
HTQTASWMFG VSPEAVDPLM RRAAKTVNFG VLYGMSAHRL SQELAIPYEE AVAFIERYFQ  420
SFPKVRAWLK KTLEEGRKRG YVETLFGRRR YVPDLNARVK SVRRRAERMA FNMPVQGTAA  480
DLMKLAMVKL FPHLREMGAR MLLQVHDELL LEAPQARAEE VAALAKEAME KAYPLAVPLE  540
VEVGIGEDWL SAKGVDGGGG SATVKFKYKG EEKEVDISKI KKVWRVGKMI SFTYDEGGGK  600
TGRGAVSEKD APKELLQMLE KQKKLEHHHH HHHH                             634

SEQ ID NO: 8            moltype = DNA   length = 424
FEATURE                 Location/Qualifiers
source                  1..424
                        mol_type = other DNA
                        organism = unidentified
SEQUENCE: 8
aggttctggt aatgacgagg cgacccgtcg taccttagct atcgctaagc tacgggaggc   60
gaatggtgat cgcggtcaga taaatagaga aggtttctta catgacaaat ccttgtcatg  120
ggatccggat gttttacaaa ccagcatccg tagccttatt ggcaacctcc tctctggcta  180
ccgatcgtcg ttgtttgggc aatgcacgtt ctccaacggt gctccatgg ggcacaagtt  240
gcaggatgca gcgccttaca agaagttcgc tgaacaagtc acgttaccc cccgcgctgt  300
gagagcggct ctattggtcc gagaccaatg tgcgccgtgg atcagacacg cggtccgcta  360
taacgagtca tatgaattta ggctcgttgt agggaacgga gtgtttacag ttccgaagaa  420
taat                                                              424

SEQ ID NO: 9            moltype = DNA   length = 40
FEATURE                 Location/Qualifiers
source                  1..40
                        mol_type = unassigned DNA
                        organism = unidentified
SEQUENCE: 9
ctcatctgag cggtgacaag aacctgattc gtgtgtttca                        40

SEQ ID NO: 10           moltype = DNA   length = 46
FEATURE                 Location/Qualifiers
source                  1..46
                        mol_type = unassigned DNA
                        organism = unidentified
SEQUENCE: 10
ctttgtgtgc ttagtccaag aacagtggcg agtctactcg gtcttg                 46

SEQ ID NO: 11           moltype = DNA   length = 42
FEATURE                 Location/Qualifiers
source                  1..42
                        mol_type = unassigned DNA
                        organism = unidentified
SEQUENCE: 11
gaaagttcgt gcgtggctca aaaaaaccct ggaagaaggt cg                     42
```

```
SEQ ID NO: 12           moltype = DNA   length = 47
FEATURE                 Location/Qualifiers
source                  1..47
                        mol_type = unassigned DNA
                        organism = unidentified
SEQUENCE: 12
gaagaaggtc ccaaaaaaac tcggtgcgtg cttgaaagcc cttcctg              47

SEQ ID NO: 13           moltype = DNA   length = 45
FEATURE                 Location/Qualifiers
source                  1..45
                        mol_type = unassigned DNA
                        organism = unidentified
SEQUENCE: 13
gttaaatctg tacgccgccg tgctgaacgt atggcattta acatg                45

SEQ ID NO: 14           moltype = DNA   length = 47
FEATURE                 Location/Qualifiers
source                  1..47
                        mol_type = unassigned DNA
                        organism = unidentified
SEQUENCE: 14
tacggtatgc aagtcgtgcc gccgcatgtc taaattgtgc gcgcaag              47

SEQ ID NO: 15           moltype = DNA   length = 46
FEATURE                 Location/Qualifiers
source                  1..46
                        mol_type = unassigned DNA
                        organism = unidentified
SEQUENCE: 15
taagaaggag atatacatat gggtctgctg cacgagtttg gcctgc               46

SEQ ID NO: 16           moltype = DNA   length = 47
FEATURE                 Location/Qualifiers
source                  1..47
                        mol_type = unassigned DNA
                        organism = unidentified
SEQUENCE: 16
gctaccaccg cccccgtcga cacctttagc gctcagccaa tcttcac              47

SEQ ID NO: 17           moltype = DNA   length = 40
FEATURE                 Location/Qualifiers
source                  1..40
                        mol_type = unassigned DNA
                        organism = unidentified
SEQUENCE: 17
gcacgttctc caacggtgct ggttgcttgt tcagcgaact                      40

SEQ ID NO: 18           moltype = DNA   length = 41
FEATURE                 Location/Qualifiers
source                  1..41
                        mol_type = unassigned DNA
                        organism = unidentified
SEQUENCE: 18
gcccaaacaa cgacgatcgg taaaaccagc atccgtagcc t                    41

SEQ ID NO: 19           moltype = DNA   length = 19
FEATURE                 Location/Qualifiers
source                  1..19
                        mol_type = unassigned DNA
                        organism = unidentified
SEQUENCE: 19
tgcaggatgc agcgcctta                                             19

SEQ ID NO: 20           moltype = DNA   length = 19
FEATURE                 Location/Qualifiers
source                  1..19
                        mol_type = unassigned DNA
                        organism = unidentified
SEQUENCE: 20
ccagagagga ggttgccaa                                             19

SEQ ID NO: 21           moltype = DNA   length = 20
FEATURE                 Location/Qualifiers
source                  1..20
                        mol_type = unassigned DNA
                        organism = unidentified
SEQUENCE: 21
caatagagcc gctctcagag                                            20
```

-continued

```
SEQ ID NO: 22          moltype = DNA  length = 20
FEATURE                Location/Qualifiers
source                 1..20
                       mol_type = unassigned DNA
                       organism = unidentified
SEQUENCE: 22
tgtcatggga tccggatgtt                                            20
```